United States Patent [19]  [11] 3,985,798
Floyd, Jr. et al.  [45] Oct. 12, 1976

[54] 11α-HOMO-PROSTANOIC ACIDS AND ESTERS

[75] Inventors: Middleton Brawner Floyd, Jr., Suffern, N.Y.; Martin Joseph Weiss, Oradell, N.J.

[73] Assignee: American Cyanamid Company, Stamford, Conn.

[22] Filed: Jan. 27, 1975

[21] Appl. No.: 544,745

[52] U.S. Cl. .............................. 260/514 D; 260/395; 260/399; 260/402; 260/410.9 R; 260/413; 260/468 D; 260/468 K; 260/470; 260/514 K; 260/516; 260/520 B; 424/305; 424/308; 424/317

[51] Int. Cl.² .................... C07C 61/38; C07C 69/74

[58] Field of Search ............... 260/514 D, 470, 516, 260/520, 468 D

[56] References Cited
UNITED STATES PATENTS

| | | | |
|---|---|---|---|
| 3,514,383 | 5/1970 | Beal et al. | 204/158 |
| 3,729,502 | 4/1973 | Beal et al. | 260/468 |
| 3,873,607 | 3/1975 | Bernardy et al. | 260/514 |
| 3,876,690 | 4/1975 | Floyd et al. | 260/514 |

Primary Examiner—Robert Gerstl
Attorney, Agent, or Firm—Edward A. Conroy, Jr.

[57] ABSTRACT

This disclosure describes 11α-homo-prostanoic acid derivatives which are useful as gastric acid secretion inhibitors.

13 Claims, No Drawings

11 α-HOMO-PROSTANOIC ACIDS AND ESTERS

BRIEF SUMMARY OF THE INVENTION

This invention relates to novel organic compounds of the 11a-homo-prostanoic acid class and more particularly is represented by the following generic formula:

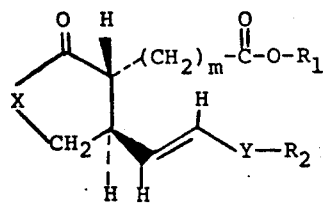

or a racemic compound of that formula and the mirror image thereof, wherein m is an integer having the value 5 to 8 inclusive; $R_1$ is hydrogen or an alkyl group of from one to twelve carbon atoms; $R_2$ is an alkyl group having from 4 to 7 carbon atoms; Y is a divalent moiety selected from the group consisting of

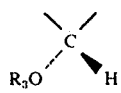

and

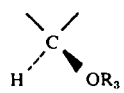

groups, wherein $R_3$ is hydrogen or triphenylmethyl; and X is a divalent moiety selected from the group consisting of

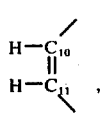 , 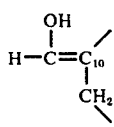

(and tautomers thereof),

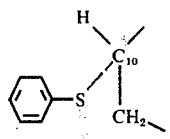 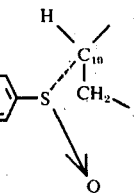

and

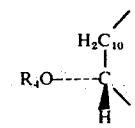

wherein $R_4$ is hydrogen or a lower alkyl group of from 1 to 3 carbon atoms and when $R_1$ is hydrogen the pharmaceutically acceptable salts thereof.

DETAILED DESCRIPTION OF THE INVENTION

The compounds of this invention are named as derivatives of 11a-homoprostanoic acid, the structure of which is shown immediately below. As shown, 11a-homoprostanoic acid has the same absolute configuration of the naturally-occurring mammallian prostaglandins.

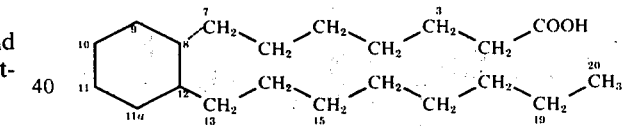

The novel compounds of this invention can be prepared by the sequence of reactions outlined in Flowsheet A which follows and wherein $R'_1$ is an alkyl group, and $R_2$ and m are as hereinabove defined.

FLOWSHEET A

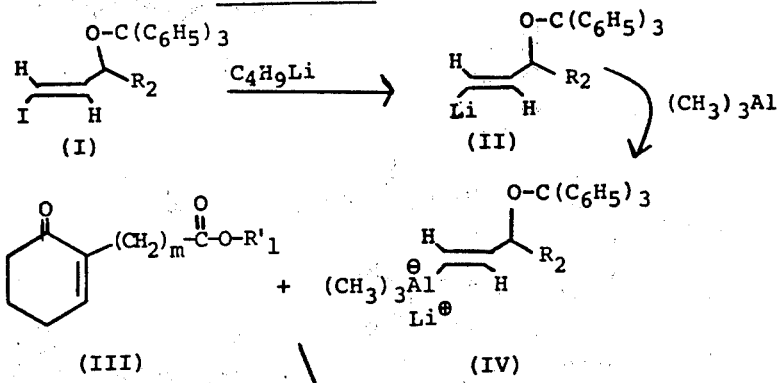

Flowsheet A—Continued
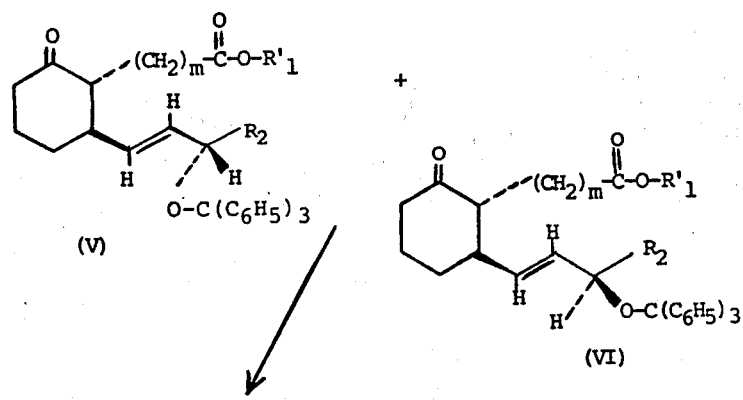
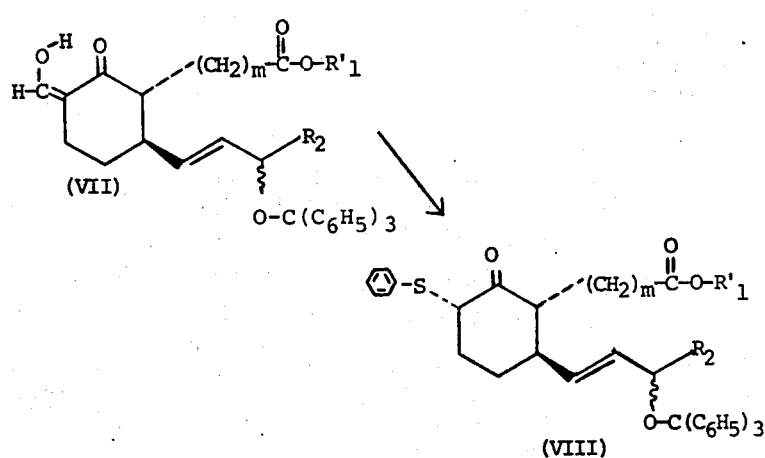
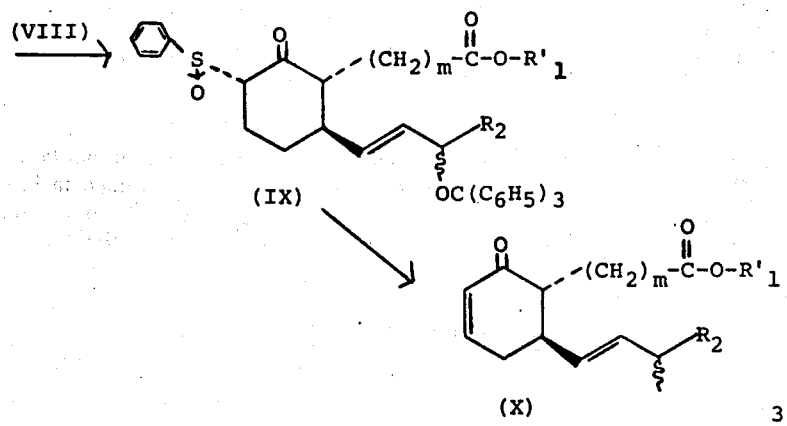
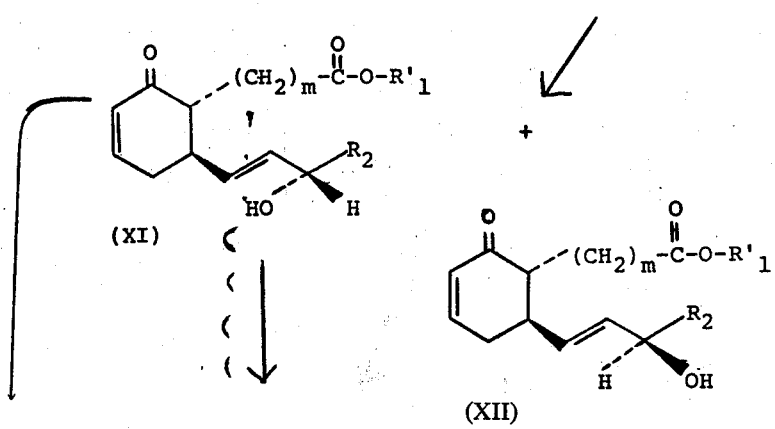

Flowsheet A - Continued

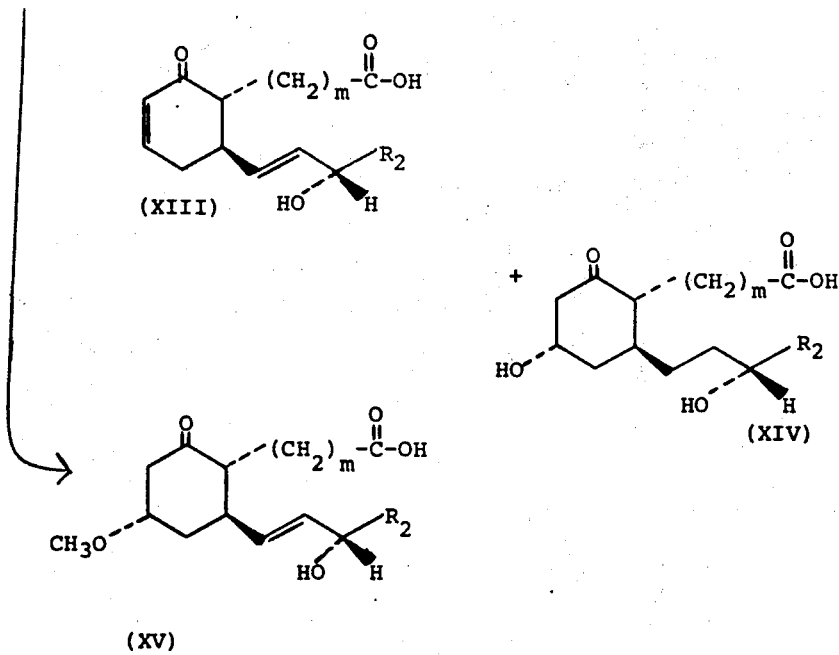

(XIII)

(XIV)

(XV)

In accordance with the sequence outlined in Flowsheet A, the 1-iodo-3-triphenylmethoxy-1-trans-alkene (I) is lithiated with retention of the trans-configuration, by treatment with n-butyl lithium at about −45° C. The resulting 1-lithio derivative (II) is treated with a trialkyl aluminum, e.g., trimethylaluminum, to give the lithio alanate (IV) which is then reacted directly with cyclohexenone (III) to give the blocked 9-keto-11-deoxy-11a-homo-15-oxy-13-trans-prostenoic acids (V) and (VI). (See Netherlands application 7310-277 (Jan. 28, 1974) (*Central Patents Index*, 13-*Farmdoc*; 10736 V/06) for the synthesis of prostenoic acids (V) and (VI) by the sequence of Flowsheet A, or by a related procedure involving the preparation of a lithio-alanate derivative corresponding to (IV) by treatment of a 3-trityloxy-1-alkyne with diisobutyl aluminum hydride followed by reaction with an alkyl lithium, e.g., methyl lithium. Also, see Netherlands application 7208576-Q (Jan. 16, 1973) (*Central Patents Index*, 13-*Farmdoc*,, 05694U-B) for the synthesis of cyclopentenones (III).

The subsequent transformations of Flowsheet A can be carried out with the racemic mixture (V) + (VI), or the individual racemates (V) or (VI), or the individual enantiomeric components of (V) or (VI). Treatment with sodium hydride and methyl or ethyl formate provides the hydroxymethylene derivative (VII), reaction of the sodium salt of which with benzenesulfenyl chloride, followed by deformylation with a base such as sodium ethoxide gives the phenylthio derivative (VIII). Preferential oxidation of (VIII) with m-chloroperoxybenzoic acid provides the corresponding sulfoxide (IX), which on heating in solution at about 80° C. eliminates benzenesulfenic acid to provide the cyclohexenone (X). Cleavage of the trityl ether with acetic acid-tetrahydrofuran-water (4:2:1) at about 45° C. for several hours provides the 15-ols (XI) and (XII), separable by chromatography. Saponification of cyclohexenone esters (XI) (or XII) in aqueous medium then gives the corresponding acid, in this instance (XIII), and the 11α-hydroxy derivative (XIV), separable by chromatographic procedures. Treatment of cyclohexenone (XI) with methanolic hydroxide gives the 11-methoxy derivative (XV).

The various carboxylic acids of this invention can be converted to the corresponding esters by the usual procedures, e.g., treatment with the appropriate diazoalkane.

The compounds of this invention can be prepared as racemic mixtures, or as single racemates or as individual diastereomers. If the 1-iodo-3-trityloxy-trans-1-alkene (I) is a non-resolved racemate, then the products of conjugate addition will be (V) and (VI), each in the racemic form. These racemates can be separated from each other by chromatographic procedures, preferably after removal of the triphenylmethyl blocking group. The separated individual racemates can then be utilized for further transformations after reblocking the 15-hydroxy function, for example with triphenylmethyl. If desired, the separation of the two racemates can be accomplished at latter stages in the sequence, for example with the 15-hydroxycyclohexenones (XI) and (XII). Again, this separation can be accomplished by chromatographic procedures.

If the initial 1-iodo-3-triphenylmethoxy alkene (I) is in the resolved form, then the separations noted above, for example (V) from (VI) or the corresponding 15-ols, or (XI) from (XII) provides the appropriate individual diastereomers. The resolved 1-iodo-3-triphenylmethoxyalkenes (I) can be obtained from the corresponding resolved 3-hydroxy-1-alkyne, from which they are readily prepared by tritylation of the hydroxy function and sequential reaction with disiamylborane, anhydrous trimethylamine oxide, aqueous sodium hydroxide solution, and iodine [see A. F. Kluge, K. G. Untch and J. H. Fried, *Jour. Amer. Chem. Soc.*, 94, 7827 (1972)]. The preparation of 3R and 3S 3-hydroxy-1-octyne has been described [(see J. Fried et al.; *Ann. N.Y. Acad. Sci.*, 180, 60(1971); R. Pappo et al., ibid., 180, 66 (1971)]. Also, 1-iodo-(3S)-3-hydroxy-trans-1-octene has been prepared (A. F. Kluge et al., loc. cit.).

The natural prostaglandins have a broad spectrum of biological properties. Because of these diverse effects their potential therapeutic use is limited. Therefore, it is particularly noteworthy that although novel compounds of this invention are prostaglandin congeners they are much more selective in their biological effects. In particular, these compounds appear to have, at most, very weak stimulating effects for smooth muscle tissue and they do not significantly effect blood pressure. On the other hand, they do inhibit gastic acid secretion and accordingly are potentially useful for the treatment of peptic ulcers, gastric hyperacidity and gastric erosion. Inhibition of basal gastric acid secretion can be determined by the following procedure. Female Sprague-Dawley rats weighing 140–160 grams are fasted in individual cages for 18–24 hours. The rats are then lightly anesthetized with ether and their front teeth extracted to avoid destruction of the plastic cannula. A midline incision is then made and the stomach and duodenum exposed. A flanged polyvinyl tube is inserted into the fundic portion of the stomach and secured with a purse string suture line using 4-0 Mersilene. The rat is then dosed by injection of the compound into the duodenum (1.0 ml. per 100 gram body weight). After dosing, the abdominal wall and skin are closed using metal wound clips. The rat is replaced in a cage containing a longitudinal slit to allow the polyvinyl tube to hang freely. An 8 ml. plastic collecting tube is attached to the flanged cannula and hangs freely below the cage. The first 30 minute sample is discarded designating this time as zero. The collecting tube is attached again and samples removed at the end of 60 and 120 minutes. These samples are referred to as A and B in the table. The hourly samples are then transferred to a 15 ml. centrifuge and centrifuged for 5–10 minutes. Total and sediment volume are then recorded with the supernatant volume being used as volume of secretion. A 1 ml. or less aliquot is then removed and placed in a 50 ml. beaker containing 10 ml. of distilled water. This sample is then titrated using 0.01N NaOH to pH 7.0 using a Beckman zeromatic pH meter, Volume, titratable acidity (meq/L), and total acid output (ueg/hour) are recorded. Percent inhibition is determined by comparison with the appropriate control. Groups of three rats were used for preliminary testing, and groups of six rats were used for dose-response evaluations. All compounds are administered in a vehicle consisting of 0.5% methocel, 0.4% Tween 80, and saline at a constant volume of 1 ml./100 gram rat. Samples are dispersed by sonification. Percent inhibition is calculated on basis of concurrent vehicle control.

In Table A which follows is given the effect on total acid output after 120 minutes of a 10 mg./kg. intraduodenal dose of representative compounds of this invention.

TABLE A

Inhibition of Total Acid Output in the Acute Gastric Fistula Rat

| Compound | % Inhibition 60"(A) | Total Acid Output 120" (B) |
|---|---|---|
| dl-11a-homoprostaglandin $A_1$ | 35 | 33 |
| dl-11a-homoprostaglandin $E_1$ | 69 | 74 |
| dl-11a-homo-15-epi-prostaglandin $A_2$ | 43 | 47 |

Certain of the novel compounds of this invention are also useful as intermediates for the preparation of other compounds of the invention.

This invention will be described in greater detail in conjunction with the following specific examples.

EXAMPLE 1

Preparation of ethyl 9-oxo-15ξ-trityloxy-11a-homo-13-trans-prostenoates

To a stirred solution of 32.3 g. (62.5 mmol) of 96% pure 1-iodo-3-trityloxy-trans-1-octene in 35 ml. of toluene is added 32.5 ml. (61.8 mmol) of 1.9M n-butyllithium in hexane during 20 minutes at ca. −65° C. The resulting solution is stirred at −40° C. for 1 hour and then treated during 10 minutes with 42 ml. (61 mmoles) of 1.446 M trimethylaluminum in hexane at −40° to −30° C. The stirred solution is allowed to warm to 10° C during 20 minutes, is recooled to 0° C., and treated during 30 minutes with a solution of 2-(6-carbethoxyhexyl)cyclohex-2-en-1-one (12.62 g., 50 mmol) in 50 ml. of ether. The resulting mixture is stirred at ambient temperature for 137 hours, diluted with ether, and poured into a stirred mixture of 750 g. of ice and 25 ml. of concentrated hydrochloride. The organic phase is washed with water and brine and dried over magnesium sulfate. The residue obtained by evaporation of solvent is subjected to dry column chromatography on silica gel with benzene as developing solvent to afford the title compound as a colorless oil in 35% yield. ir (film: 5.75, 5.83, and 10.65μ. pmr (CCl$_4$): δ3.74 (1, m, CHO).

EXAMPLE 2

Preparation of ethyl 9-oxo-15ξ-hydroxy-11a-homo-13-trans-prostenoates

A solution of 5.6 g. (9.0 mmol) of ethyl 9-oxo-15ξ-trityloxy-11a-homo-13-trans-prostenoate (Example 1) in 180 ml. of 4:2:1 HOAc—THF — H$_2$O is heated under nitrogen for 4 hours at 45° C. The solvents are removed at reduced pressure. The resulting mixture is slurried with 100 ml. of 20:1 petroleum ether — EtOAc, and the mixture is cooled and filtered to remove triphenylcarbinol. The filtrate is concentrated, and the residue is subjected to dry column chromatography on silica gel with 5:1 benzene-EtOAc as developing solvent. In this way, the following components are separated:

The more polar component, ethyl 9-oxo-15-hydroxy-11a-homo-13-trans-prostenoate is isolated as an oil, 995 mg.; ir (film): 5.75, 5.84, and 10.33μ.

The less polar component, ethyl 9-oxo-15-epi-hydroxy-11a-homo-13-trans-prostenoate, is isolated as an oil, 641 mg.; ir (film): 5.75, 5.84, and 10.33μ.

EXAMPLE 3

Preparation of 9-oxo-15-hydroxy-11a-homo-13-trans-prostenoic acid

To a stirred solution of 780 mg. (2.05 mmol) of ethyl 9-oxo-15-hydroxy-11a-homo-13-trans-prostenoate (Example 2) in 12 ml. of 10:1 methanol-water is added 345 mg. of potassium hydroxide. After solution is complete the solution is allowed to stand under nitrogen for 28 hours at room temperature. The solution is diluted with 35 ml. of water and extracted with ether. The aqueous phase is acidified with 2.0 ml. of 4N HCl, saturated with NaCl, and extracted with ether. The extract is washed with brine, dried over magnesium sulfate, and evaporated to give 700 mg. of crystalline product, m.p. 94°–97° C. after recrystallization from 1:1 ether-petroleum ether; ir (KBr): 5.78, 5.92, and 10.28μ. pmr (acetone-d$_6$): 5.50 (2, m, C$\underline{H}$=C$\underline{H}$) and 4.04 (1, m, C$\underline{H}$O).

EXAMPLE 4

Preparation of 9-oxo-15-epi-hydroxy-11a-homo-13-trans-prostenoic acid

In the manner of Example 3, ethyl 9-oxo-15-epi-hydroxy-11a-homo-13-trans-prostenoate (Example 2) is saponified to give an oil; ir (film): 5.83 and 10.32μ. pmr (acetone-d$_6$): δ5.50 (2, m, C$\underline{H}$=C$\underline{H}$) and 4.04 (1, m, C$\underline{H}$O).

EXAMPLE 5

Preparation of ethyl 10-hydroxymethylene-9-oxo-15ξ-trityloxy-11a-homo-13-trans-prostenoate To a stirred suspension of sodiumhydride (prepared by washing 195 mg. of 57% dispersion with petroleum ether) in 3 ml. of ethyl formate is added solution of 721 mg. (1.16 mmol) of ethyl 9-oxo-15-ξ-trityloxy-11a-homo-13-trans-prostenoate (Example 1) in 5 ml. of glyme. Hydrogen gas is evolved, and after 75 minutes the solution is poured into 10 ml. of half-saturated aqueous ammonium chloride. The mixture is extracted with ether. The extract is washed with brine, dried over magnesium sulfate, and evaporated. The residue is purified by preparative TLC to provide a viscous oil, uv (MEOH): λmax 205(16500) and 300 mμ (5200); (dil. KOH in MEOH): λmax 205 (20300) and 317 mμ (15000).

EXAMPLE 6

Preparation of ethyl 10-phenylthio-9-oxo-15ξ-trityloxy-11a-homo-13-trans-prostenoate To a stirred suspension of sodium hydride (prepared by washing 371 mg. of 57% dispersion with petroleum ether) in 32 ml. of benzene is added a solution of 5.27 g. (maximum of 7.88 mmoles) of crude ethyl 10-hydroxymethylene-9-oxo-15ξ-trityloxy-11a-homo-13-trans-prostenoate (Example 5) in 80 ml. of benzene. Reaction is initiated by the addition of a trace of ethanol.

After 1 hour at room temperature the stirred solution of the sodium salt is treated during 2 minutes with a solution of 1.25 g. (8.07 mmoles) of benzenesulfenyl chloride in 8 ml. of benzene. After 10 minutes the mixture is treated with sodium bicarbonate solution and diluted with ether. The organic phase is separated and washed successively with water and brine, dried over magnesium sulfate, and concentrated to give a mixture of the title compound and its 3-formyl derivative.

Deformylation is completed by dissolving the mixture in 75 ml. of ethanol and treating the solution with 10 ml. of 0.1N sodium ethoxide in ethanol. After 4 hours at room temperature the solution is treated with 90 mg. (1.5 mmol) of HOAc and evaporated with aid of toluene to give 6.50 g. of viscous amber oil; ir (film): 5.79 and 5.87μ.

EXAMPLE 7

Preparation of ethyl 10-phenylsulfinyl-9-oxo-15ξ-trityloxy-11a-homo-13-trans-prostenoate To a stirred ice-cold solution of 6.50 g. (maximum of 7.88 mmol) of crude ethyl 10-phenylthio-9-oxo-15ξ-trityloxy-11a-homo-13-trans-prostenoate (Example 6) in 85 ml. of chloroform is added a solution of 1.71 g. (8.42 mmol) of 85% m-chloroperoxybenzoic acid in 50 ml. of chloroform during 60 minutes. After stirring at 0° C. for 15 minutes the solution is treated with 50 ml. of half-saturated aqueous sodium sulfite. After 5 minutes the mixture is diluted with chloroform. The organic phase is separated, washed successively with sodium bicarbonate solution and water, and dried over magnesium sulfate. Evaporation gives 6.41 g. of light amber gum; ir (film): 5.81, 5.90, and 9.70μ.

EXAMPLE 8

Preparation of ethyl 9-oxo-15ξ-trityloxy-11a-homo-10,13-trans-prostadienoiate

A stirred solution of 6.40 g. (maximum of 7.85 mmol) of crude ethyl 10-phenylsulfinyl-9-oxo-15ξ-trityloxy-11a-homo-13-trans-prostenoiate (Example 7) in 160 ml. of benzene is refluxed for 3 hours. The solution is concentrated and the residue is slurried with 125 ml. of 30:1 petroleum ether-ethyl acetate. The filtrate is concentrated to give an oil; ir (film) = 5.83, 6.03, and 6.35μ.

EXAMPLE 9

Preparation of ethyl 9-oxo-15ξ-hydroxy-11a-homo-10,13-transprostadienoates

A solution of 6.35 g. (maximum of 7.85 mmol) of ethyl 9-oxo-15ξ-trityloxy-11a-homo-10,13-trans-prostadienoate (Example 8) in 160 ml. of 4:2:1 HOAc—THF—H$_2$O is heated at 45° C. for 8 hours. The solvents are removed at reduced pressure with the aid of toluene to give a mixture of oil and crystalline triphenylcarbinol.

This residue is dissolved in 10 ml. of 30:20:1 heptane-ethyl acetate-HOAc and subjected to dry column chromatographic separation on silica gel using the same solvent.

The more polar component, ethyl 9-oxo-15-hydroxy-11a-homo-10,13-trans-prostadienoate, is obtained as an oil, 1.058 g.; ir (film): 5.77, 5.98, and 10.32μ.

The less polar component, ethyl 9-oxo-15-epihydroxy-11a-homo-10,13-trans-prostadienoate is obtained as an oil, 1.047 g.; ir (film): 5.77, 5.98, and 10.32μ.

EXAMPLE 10

Preparation of 9-oxo-15-hydroxy-11a-homo-10,13-trans-prostadienoic acid and 9-oxo-11α,15-dihydroxy-11a-homo-13-trans-prostenoic acid To a stirred solution of 1.058 g. (2.79 mmol) of ethyl 9-oxo-15-hydroxy-11a-homo-10,13-trans-prostadienoate (Example 9) in 20 ml. of methanol and 10 ml. of water is added 470 mg. (8.4 mmol) of potassium hydroxide. The resulting solution is allowed to stand at room temperature for 19 hours. The methanol is evaporated from the mixture at reduced pressure and replaced with water to give an aqueous solution. After 4 hours reaction at room temperature the solution is acidified with 2.5 ml. of 4N HCl, saturated with sodium chloride, and extracted with ethyl acetate. The extract is washed with brine, dried over magnesium sulfate, and concentrated.

The residue is dissolved in 3 ml. of 100:1 ethyl acetate - HOAc and subjected to dry column chromatographic separation on silica gel using the same solvent.

The less polar component, 9-oxo-15-hydroxy-11a-homo-10,13-trans-prostadienoic acid, is obtained as white crystals, m.p. 86°–92° C. after recrystallization from ether-petroleum ether ir (KBr): 5.78, 6.03, and 10.23μ. pmr (CDCl₃): 6.86 (1, m, 11-H), 5.96 (1, d, 10-H), 5.58 (2, m, 13-H and 14-H) and 4.08 (1, m, CHO). uv (MeOH): λmax. 223 mμ (7700).

The more polar component, 9-oxo-11α,15-dihydroxy-11a-homo-13-trans-prostenoic acid, is obtained as white crystals, m.p. 77°–81° C. after recrystallization from ethyl acetate-petroleum ether; pmr (acetone-d₆): δ5.50 (2, m, 13-H and 14-H), 4.37 (1, m, 11β-H), and 4.06 (1, m, 15-H).

EXAMPLE 11

Preparation of
9-oxo-15-epi-hydroxy-11a-homo-10,13-trans-prostadienoic acid and
9-oxo-11α,15-epi-dihydroxy-11a-homo-13-trans-prostenoic acid In the manner of Example 10, ethyl 9-oxo-15-epi-hydroxy-11a-homo-10,13-trans-prostadienoate (Example 9) is converted to a mixture of the title compounds by successive treatment with aqueous-methanolic potassium hydroxide and aqueous potassium hydroxide.

EXAMPLE 12

Preparation of
9-oxo-11α-methoxy-15-epi-hydroxy-11a-homo-13-trans-prostenoic acid A stirred solution of 1.047 g. (2.76 mmol) of ethyl 9-oxo-15-epi-hydroxy-11a-homo-10,13-trans-prostadienoic (Example 9) in 18 ml. of 10:1 methanol-water is treated with 436 mg. of potassium hydroxide. The resulting solution is allowed to stand at room temperature for 20 hours, diluted with water, and extracted with ether. The aqueous phase is acidified with hydrochloric acid and extracted with ether and ethyl acetate. The extract is washed with brine, dried over magnesium sulfate and concentrated.

The residue is dissolved in 100:1 ethyl acetate-HOAc and subjected to thin layer chromatography on silica gel. The more polar component is obtained as an oil; pmr (CDCl₃): δ4.1 (2, m, 11-H and 15-H) and 3.3 (3, s, OCH₃).

We claim:

1. An optically active compound of the formula:

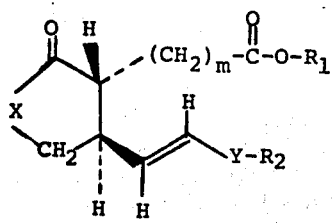

or a racemic compound of that formula and the mirror image thereof wherein m is an integer from 5 to 8, inclusive; $R_1$ is selected from the group consisting of hydrogen and alkyl of one to twelve carbon atoms; $R_2$ is alkyl of four to seven carbon atoms; Y is a divalent moiety selected from the group consisting of:

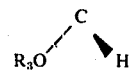

and

wherein $R_3$ is selected from the group consisting of hydrogen and triphenylmethyl; and X is a divalent moiety selected from the group consisting of:

and tautomers thereof,

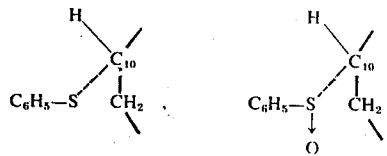

and

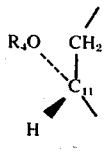

wherein $R_4$ is selected from the group consisting of hydrogen and alkyl of one to three carbon atoms; and the pharmacologically acceptable cationic salts thereof when $R_1$ is hydrogen.

2. The optically active compound according to claim 1 wherein m is 6, $R_1$ is hydrogen, $R_2$ is n-pentyl, Y is

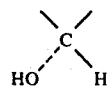

X is

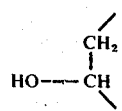

1-9-oxo-11α,15-dihydroxy-11a-homo-13-trans-prostenoic acid.

3. The optically active compound according to claim 1 wherein $m$ is 6, $R_1$ is hydrogen, $R_2$ is n-pentyl, Y is

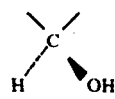

X is

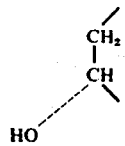

1-9-oxo-11α,15-epi-dihydroxy-11a-homo-13-trans-prostenoic acid.

4. The optically active compound according to claim 1 wherein $m$ is 6, $R_1$ is hydrogen, $R_2$ is n-pentyl, Y is

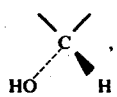

X is

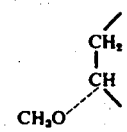

1-9-oxo-11α-methoxy-15-hydroxy-11a-homo-13-trans-prostenoic acid.

5. The optically active compound according to claim 1 wherein $m$ is 6, $R_1$ is hydrogen, $R_2$ is n-pentyl, Y is

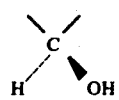

X is

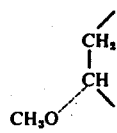

1-9-oxo-11α-methoxy-15-epi-hydroxy-11a-homo-13-trans-prostenoic acid.

6. The optically active compound according to claim 1 wherein $m$ is 6, $R_1$ is hydrogen, $R_2$ is n-pentyl, Y is

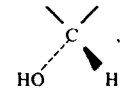

X is

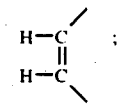

1-9-oxo-15-hydroxy-11a-homo-10,13-trans-prostadienoic acid.

7. The optically active compound according to claim 1 wherein $m$ is 6, $R_1$ is hydrogen, $R_2$ is n-pentyl, Y is

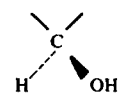

X is

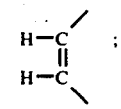

1-9-oxo-15-epi-hydroxy-11a-homo-10,13-trans-prostadienoic acid.

8. The optically active compound according to claim 1 wherein $m$ is 6, $R_1$ is hydrogen, $R_2$ is n-pentyl, Y is

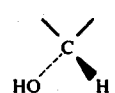

X is

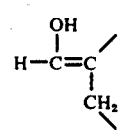

1-9-oxo-10-hydroxymethylene-15-hydroxy-11a-homo-13-trans-prostenoic acid and the tautomer thereof.

9. The optically active compound according to claim 1 wherein $m$ is 6, $R_1$ is hydrogen, $R_2$ is n-pentyl, Y is X is

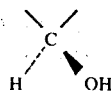

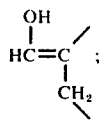

1-9-oxo-10-hydroxymethylene-15-epi-hydroxy-11a-homo-13-trans-prostenoic and the tautomer thereof.

10. The optically active compound according to claim 1 wherein $m$ is 6, $R_1$ is hydrogen, $R_2$ is n-pentyl; Y is

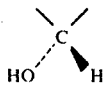

X is

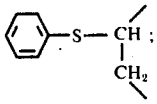

1-9-oxo-10α-phenylthio-15-hydroxy-11a-homo-13-trans-prostenoic acid.

11. The optically active compound according to claim 1 wherein $m$ is 6, $R_1$ is hydrogen, $R_2$ is n-pentyl; Y is

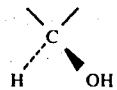

X is

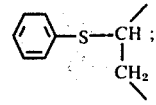

1-9-oxo-10α-phenylthio-15-epi-hydroxy-11a-homo-13-trans-prostenoic acid.

12. The optically active compound according to claim 1 wherein $m$ is 6, $R_1$ is hydrogen, $R_2$ is n-pentyl, Y is

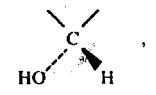

X is

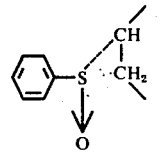

1-9-oxo-10α-homo-13-trans-prostenoic acid.

13. The optically active compound according to claim 1 wherein $m$ is 6, $R_1$ is hydrogen, $R_2$ is n-pentyl, Y is

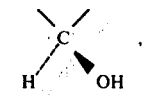

X is

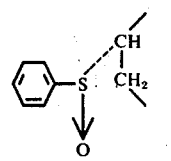

1-9-oxo-10α-homo-13-trans-prostenoic acid.

* * * * *

UNITED STATES PATENT OFFICE
CERTIFICATE OF CORRECTION

Patent No. 3,985,798    Dated October 12, 1976

Inventor(s) Middleton Brawner Floyd, Jr. and Martin Joseph Weiss

It is certified that error appears in the above-identified patent and that said Letters Patent are hereby corrected as shown below:

Section [21], "Appl. No.: 544,745" should be
-- Appl. No.: 544,475 --.

Signed and Sealed this

Fourteenth Day of December 1976

[SEAL]

Attest:

RUTH C. MASON
*Attesting Officer*

C. MARSHALL DANN
*Commissioner of Patents and Trademarks*